US011307162B2

(12) United States Patent
Yan et al.

(10) Patent No.: US 11,307,162 B2
(45) Date of Patent: Apr. 19, 2022

(54) HIGHLY SENSITIVE BIOMARKER BIOSENSORS BASED ON ORGANIC ELECTROCHEMICAL TRANSISTORS

(71) Applicant: THE HONG KONG POLYTECHNIC UNIVERSITY, Hong Kong (CN)

(72) Inventors: Feng Yan, Hong Kong (CN); Ying Fu, Hong Kong (CN)

(73) Assignee: THE HONG KONG POLYTECHNIC UNIVERSITY, Hong Kong (CN)

( * ) Notice: Subject to any disclaimer, the term of this patent is extended or adjusted under 35 U.S.C. 154(b) by 352 days.

(21) Appl. No.: 16/543,657

(22) Filed: Aug. 19, 2019

(65) Prior Publication Data

US 2020/0072780 A1 Mar. 5, 2020

Related U.S. Application Data

(60) Provisional application No. 62/719,731, filed on Aug. 20, 2018.

(51) Int. Cl.
*G01N 27/27* (2006.01)
*G01N 27/414* (2006.01)
*C12Q 1/6886* (2018.01)
*G01N 27/327* (2006.01)

(52) U.S. Cl.
CPC .......... *G01N 27/27* (2013.01); *C12Q 1/6886* (2013.01); *G01N 27/3272* (2013.01); *G01N 27/3275* (2013.01); *G01N 27/4145* (2013.01)

(58) Field of Classification Search
None
See application file for complete search history.

(56) References Cited

PUBLICATIONS

L. Caizhi, Thesis "High Performance Biological Sensors Based on Organic Electrochemical Transistors (OECTS)", The Hong Kong Polytechnic University (Year: 2014).*
J. Lin, et al. "Electrochemical and chemiluminescent immunosensors for tumor markers", Biosensors & Bioelectronics, 20(8): p. 1461-1470, Feb. 2005.*
Azaharali et al.; Microfluidic Immuno-Biochip for Detection of Breast Cancer Biomarkers Using Hierarchical Composite of Porous Graphene and Titanium Dioxide Nanofibers; ACS Applied Materials & Interfaces; 2016; pp. 20570-20582; vol. 8, Issue 32; ACS Publications.
Payne et al.; Automated Assay for HER-2/neu in Serum; Clinical Chemistry; 2000; pp. 175-182; vol. 46, Issue 2; American Association for Clinical Chemistry.

(Continued)

*Primary Examiner* — J. Christopher Ball
(74) *Attorney, Agent, or Firm* — Spruson & Ferguson (Hong Kong) Limited

(57) ABSTRACT

The present technology for the detection and analysis of analytes within a sample is based on molecular biology methods, including western blotting, gel electrophoresis, mass spectrometry, enzyme-linked immunosorbent assays and RT-PCR, which are normally time-consuming and laborious. The present disclosure provides novel OECT based electrochemical biosensors that can enable the convenient and cost-effective determination of analytes within a sample with high sensitivity and selectivity.

21 Claims, 15 Drawing Sheets

(56) References Cited

PUBLICATIONS

Van de Vijver et al.; Neu-Protein Overexpression in Breast Cancer; The New England Journal of Medicine; 1988; pp. 1239-1245; vol. 319, No. 19; Massachusetts Medical Society.

Somlo et al.; Multiple biomarker expression on circulating tumor cells in comparison to tumor tissues from primary and metastatic sites in patients with locally advanced/inflammatory, and stage IV breast cancer, using a novel detection technology; Breast Cancer Res Treat; 2011; pp. 155-163; vol. 128, Issue 1; Springer.

Yolken; Enzyme Immunoassays for the Detection of Infectious Antigens in Body Fluids: Current Limitations and Future Prospects; Reviews of Infectious Diseases; 1982; pp. 35-68; vol. 4, No. 1; Oxford University Press.

Frens et al.; Controlled nucleation for the regulation of the particle size in monodisperse gold suspensions; Nature Physical Science; 1973; pp. 20-22; vol. 241; Nature Research.

\* cited by examiner

HIGHLY SENSITIVE BIOMARKER BIOSENSORS BASED ON ORGANIC ELECTROCHEMICAL TRANSISTORS

CROSS-REFERENCES TO RELATED APPLICATIONS

This application claims priority to U.S. Provisional Application No. 62/719,731, filed Aug. 20, 2018, the entire content of which is incorporated by reference herein for all purposes.

FIELD OF THE INVENTION

The present disclosure generally relates to highly sensitive electrochemical biosensors based on organic electrochemical transistors (OECTs), and methods for the use thereof.

BACKGROUND OF THE INVENTION

Present technology for the analysis of biomarkers is based on molecular biology methods, including western blotting, gel electrophoresis, mass spectrometry, enzyme-linked immunosorbent assays and reverse transcription polymerase chain reaction (RT-PCR), all of which are normally time-consuming and laborious.

For example, western blotting is a general method to specifically detect the existence of a single protein in a mixture. A semi-quantitative estimation of a protein can be derived from the size and color intensity of a protein band on the blot membrane. Protein gel electrophoresis is a method for the separation and analysis of the proteins in a fluid or an extract. Its selectivity is based on the different electrophoretic mobilities of proteins, which are caused by the length and charge of different polypeptide chains. The two aforementioned methods both have disadvantages including: the length of time required for the procedures, low selectivity and low sensitivity. These methods are not suitable for early disease detection since the biomarker concentration change is very small.

Mass spectrometry is an analytical technique that ionizes chemical species and sorts the ions based on their mass-to-charge ratio. In a typical mass spectrometry procedure, the sample is ionized first and these ions are then separated according to their mass-to-charge ratio. The ions are detected by a mechanism capable of detecting charged particles, such as an electron multiplier. Results are displayed as spectra of the relative abundance of detected ions as a function of the mass-to-charge ratio. The atoms or molecules in the sample can be identified through a fragmentation pattern. Mass spectrometry requires complex and expensive instruments and experienced researchers to operate the instruments and to analyze the results. It also involves a devastating sample preparation process and therefore it is not suitable for the analysis of living cells.

An enzyme-linked immunosorbent assay is a test that uses antibodies and color change to identify a substance. It requires a complex detection process with limited sensitivity, which affects its suitability for clinical application.

RT-PCR is a technique commonly used to qualitatively detect gene expression in molecular biology. In RT-PCR, the RNA samples react with reverse transcriptase to produce complementary DNA (cDNA). Exponential amplification cycles are then conducted to amplify cDNA fragments so that they can be identified by available substrates. The process is very complex and has low selectivity.

There is therefore a need to develop a highly sensitive, low-cost, and simple method/device to detect specific analytes within a sample.

SUMMARY OF THE INVENTION

The present invention meets at least one of the needs mentioned above by providing devices and methods for the highly sensitive detection of analytes within a sample.

In a first aspect, the present invention provides an electrochemical biosensor comprising a plurality of electrodes, comprising:
a gate electrode comprising a first agent capable of specifically binding to an analyte;
a source electrode;
a drain electrode;
a channel comprising an organic semiconductor between the source electrode and the drain electrode;
a plurality of nanoparticles comprising an electrochemically active enzyme and a second agent capable of specifically binding to an analyte in a sample; and
a substrate for the electrochemically active enzyme,
wherein the gate electrode and the channel are separated by an electrolyte, and wherein the electrolyte contacts the gate electrode and the channel.

In some embodiments of the first aspect, the first agent and/or the second agent is an antibody.

In additional embodiments, the first agent is a monoclonal antibody capable of specifically binding to the analyte.

In further embodiments, the first agent is a nucleic acid probe which is capable of specifically binding to the analyte.

In some embodiments, the second agent is a polyclonal antibody capable of specifically binding to the analyte.

In additional embodiments, the electrochemically active enzyme is horseradish peroxidase and the substrate for the electrochemically active enzyme is hydrogen peroxide.

In some embodiments, the organic semiconductor comprises a film coating on the drain and source electrodes.

In further embodiments of the present invention, the organic semiconductor comprises poly (3,4-ethylenedioxythiophene) polystyrene sulfonate (PEDOT:PSS).

In some embodiments, at least one of the plurality of electrodes and/or the plurality of nanoparticles further comprises gold.

In additional embodiments, the gate electrode comprises grooves comprising the first agent capable of specifically binding to an analyte.

In some embodiments, the nanoparticles have a diameter of under 90 nm, under 80 nm, under 70 nm, under 60 nm, under 50 nm, under 40 nm, under 30 nm, under 20 nm, under 10 nm, or under 1 nm.

In further embodiments, the channel has a width of 5 mm and a length of 0.1 mm.

In additional embodiments, the gate electrode has a surface area that is under 100 times, under 90 times, under 80 times, under 70 times, under 60 times, under 50 times, under 40 times, under 30 times, under 20 times, under 10 times, under 5 times or under 2 times the surface area of the channel.

In some embodiments, the sample is a cell lysate.

In further embodiments, the sample is whole cells.

In additional embodiments, the analyte is protein.

In some other embodiments, the analyte is nucleic acid.

In some embodiments, the analyte is microRNA (miRNA).

In a second aspect, the present invention also provides a method for detecting an analyte in a sample, the method comprising contacting the sample in the electrochemical biosensor according to the first aspect of the present invention to produce a measurable signal.

In some embodiments, the detecting further comprises contacting a control sample in the electrochemical biosensor according to the first aspect of the present invention to produce a measurable signal and comparing the measurable signal of the sample with the measurable signal of the control sample.

In some additional embodiments, the analyte is a biomarker and the detecting comprises the diagnosis and/or prognosis of a disease and/or medical condition.

In some further embodiments, the disease and/or medical condition is cancer.

In some embodiments, the cancer is breast cancer.

In additional embodiments, the biomarker is human epidermal growth factor receptor 2 (HER2).

DEFINITIONS

Certain terms are used herein which shall have the meanings set forth as follows.

As used in this application, the singular form "a", "an" and "the" include plural references unless the context clearly dictates otherwise. For example, the term "nanoparticle" also includes a plurality of nanoparticles unless otherwise stated.

As used herein, the term "comprising" means "including". Variations of the word "comprising", such as "comprise" and "comprises" have correspondingly varied meanings. Thus, for example, a nanoparticle "comprising" may consist exclusively of or may include one or more additional components.

As used herein, the term "plurality" means more than one. In certain specific aspects or embodiments, a plurality may mean 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or more, and any numerical value derivable therein, and any range derivable therein.

As used herein, the term "between" when used in reference to a range of numerical values encompasses the numerical values at each endpoint of the range.

As used herein, the term "gate electrode", also known in the field as the reference electrode, refers to the electrode that controls the flow of electrical current between the source and drain electrodes.

As used herein, the terms "source electrode" and "drain electrode" refer to the electrodes that transmit and receive the electrical current respectively across the organic semiconductor.

BRIEF DESCRIPTION OF DRAWINGS

The above and other aspects and embodiments of the present disclosure will become apparent from the following description of the disclosure, when taken in conjunction with the accompanying drawings, in which.

DETAILED DESCRIPTION OF THE INVENTION

The present invention is not to be limited in scope by any of the specific embodiments described herein. The following embodiments are presented for exemplification only.

Figure 1:
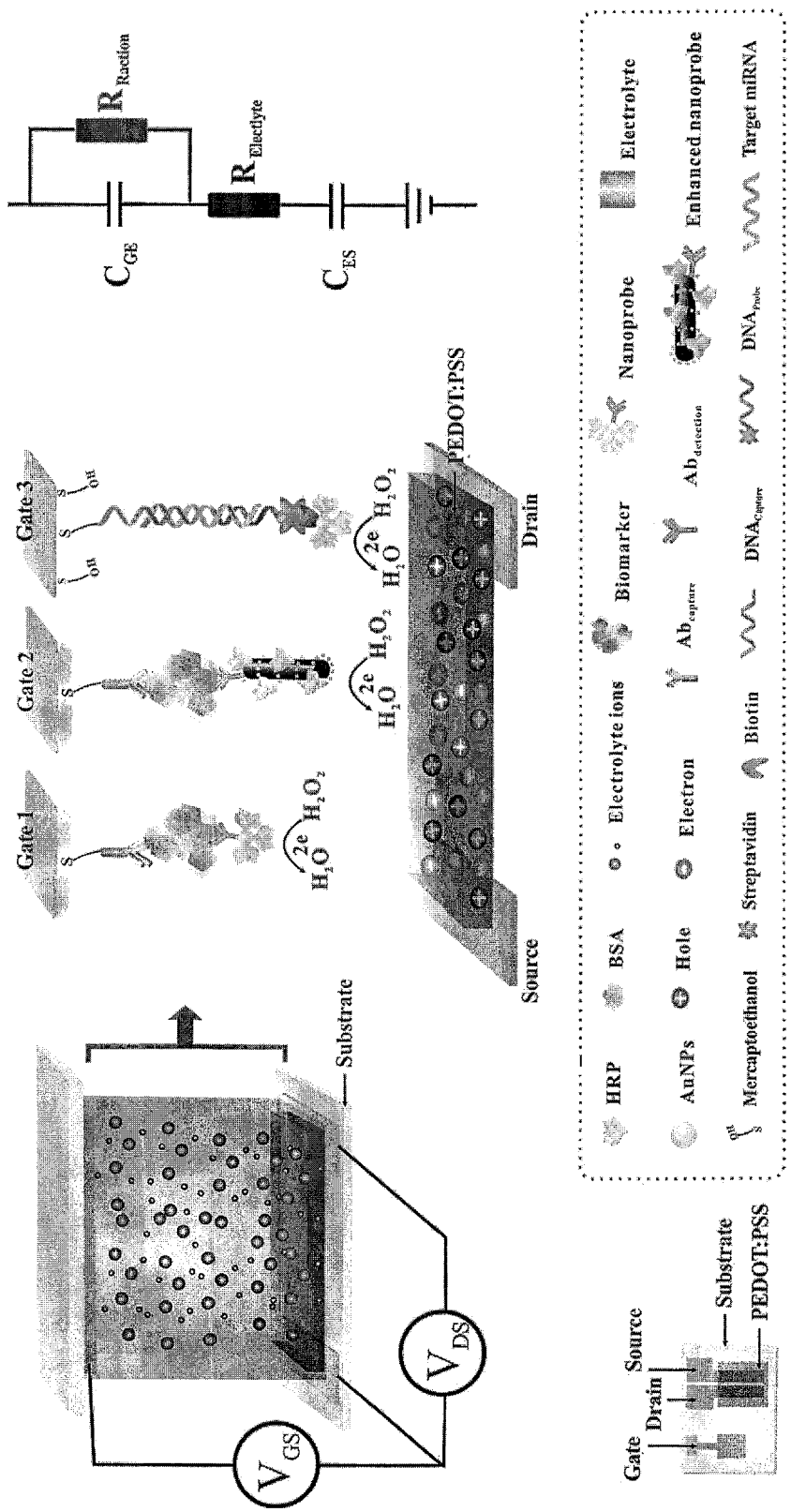
FIG. 1 provides a representative scheme of the electrochemical biosensor for the detection of a breast cancer cell biomarker. Left: OECTs with functionalized gates characterized in liquid electrolytes. Middle: Three types of modified gate electrodes to detect a protein biomarker, protein biomarker with an enhanced nanoprobe and a microRNA (miRNA) in a sample. Right: The equivalent circuit between the gate electrode and the channel of an OECT in an electrolyte. $C_{GE}$ and $C_{EC}$ correspond to the capacitances of the two electric double layers at the gate/electrolyte interface and the electrolyte/channel interface, respectively.

Herein are presented OECT-based sensors for the detection of analytes in a sample with ultrahigh sensitivity based on a novel mechanism. FIG. 1 shows an exemplary design of an OECT for the detection of various biomarkers. The drain and source electrodes are coated with poly (3,4-ethylenedioxythiophene) polystyrene sulfonate (PEDOT:PSS) film as channel; the gate electrodes are modified to detect different biomarkers. Gate 1 is modified with an antibody ($Ab_{Capture}$) that is used to capture protein biomarkers in solutions. Gate 2 is modified with an enhanced nanoprobe using an amplification strategy. Gate 3 is modified with 3'-SH modified capture DNA to capture target miRNA, and probe DNA and nanoprobes can be sequentially incubated on the electrode surface. The nanoprobes possess high electrochemical activity, which can effectively catalyse the oxidation reaction of the added hydrogen peroxide ($H_2O_2$) to generate an electrochemical signal.

Figure 9:
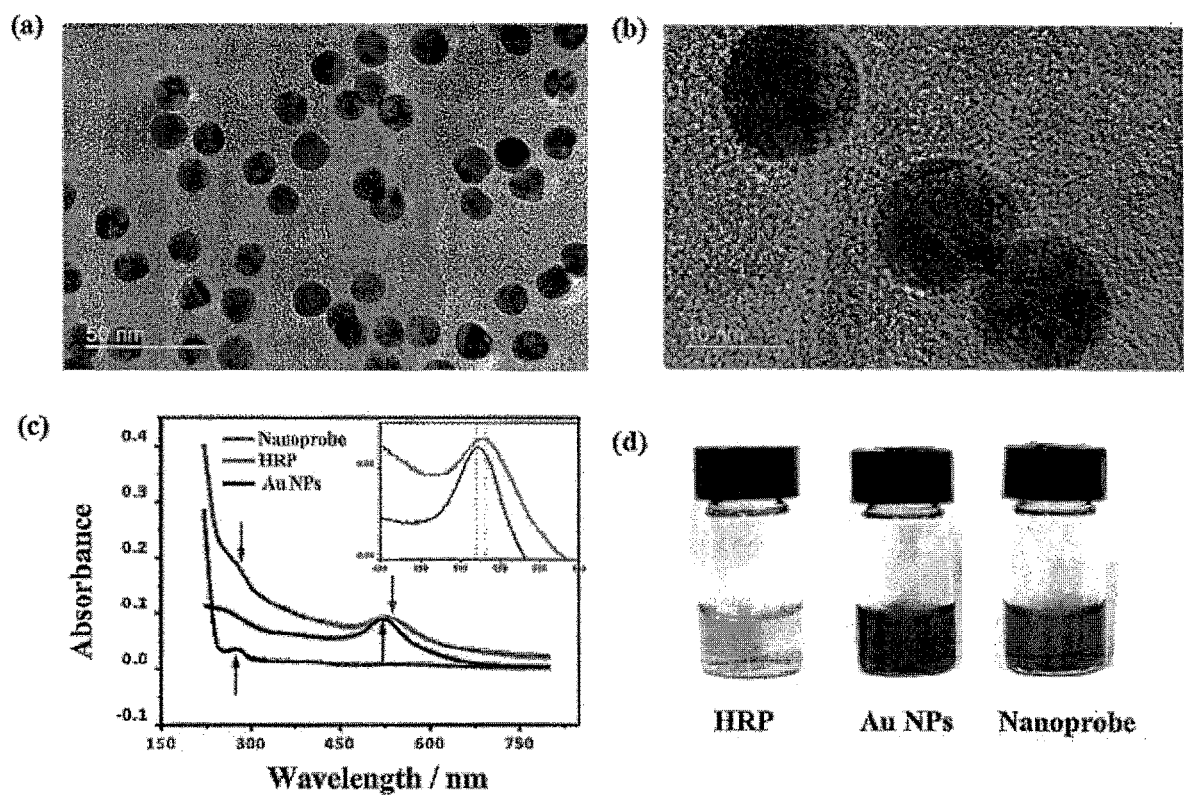
FIG. 9. Characterization of nanoprobes. (a) and (b) TEM images of Au nanoparticles (Au NPs). (c) UV-vis absorption spectra and (d) images of solutions of nanoprobes, Au NPs and HRP. The absorption peak is due to the plasmonic effect of the Au nanoparticles.

In one exemplary embodiment, the nanoprobes are Au nanoparticles (Au NPs) with a diameter of about 10 nm, which are modified with a detection antibody $Ab_{Detection}$ and an electrochemically active enzyme, horseradish peroxidase (HRP) (FIG. 9). Because the HRP enzyme can catalyse the electrochemical reaction of $H_2O_2$, the amount of HRP on the gate electrode can be characterized by adding $H_2O_2$ in a phosphate buffered saline (PBS) solution. The following reaction is catalysed by the HRP enzyme:

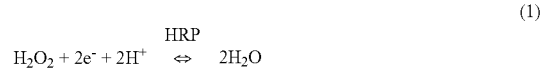

$$H_2O_2 + 2e^- + 2H^+ \xrightarrow{HRP} 2H_2O \quad (1)$$

Under a bias voltage, the redox current on the electrode should be proportional to the amount of HRP on the electrode surface. Assuming that the redox current is very low and not limited by the mass transfer of $H_2O_2$, the electrode current density i is given by the equation:

$$i = W_{HRP} i_0 e^{\alpha \eta} \quad (2)$$

Where $i_0$ is the exchange current per unit amount of HRP, η is the applied overpotential, α is constant, and $W_{HRP}$ is the amount of HRP modified on the gate. Since the OECT is a potentiometric transducer, the redox current on the gate electrode is very low and limited by the leakage across the interface between the electrolyte and the PEDOT:PSS active layer. Consequently, the potential change on the gate surface induced by the reaction of $H_2O_2$ is given by:

$$\Delta V_G \propto -\frac{1}{\alpha} \log[W_{HRP}] \quad (3)$$

According to the device physics of OECTs, the change of the effect gate voltage $V_G^{eff}$ of the transistor is thus given by:

$$\Delta V_G^{eff} \propto \left(1 + \frac{C_{EC}}{C_{GE}}\right) \frac{1}{\alpha} \log[W_{HRP}] \quad (4)$$

Where $C_{GE}$ and $C_{EC}$ are the capacitances of the two electric double layers on the gate and the channel, respectively. Therefore, in the characterization of the protein sensors, one solution containing target proteins was used to modify the gate electrode and another standard PBS solution with an addition of $H_2O_2$ was used for measuring the concentration of HRP enzyme.

Figure 2:
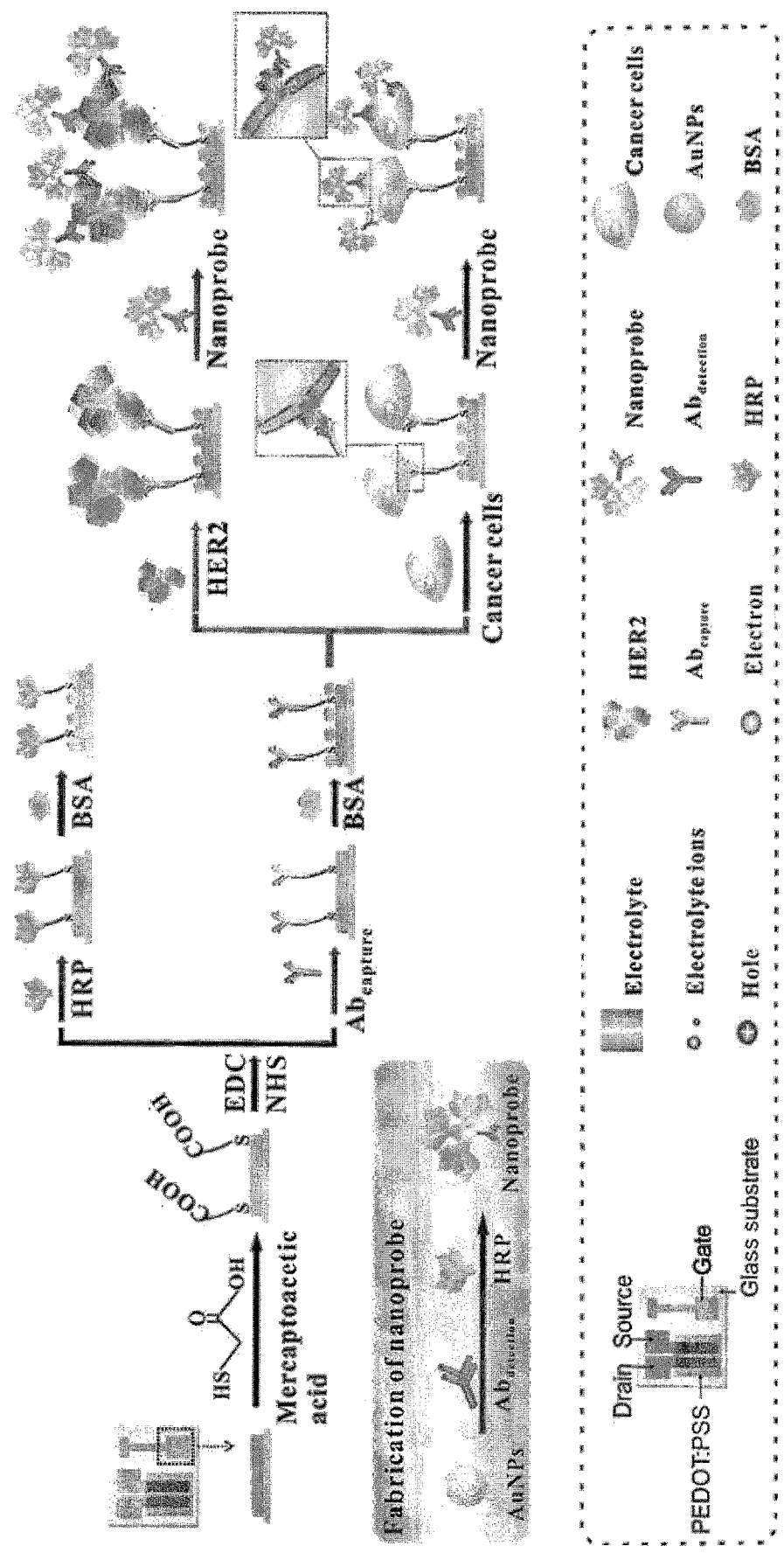
FIG. 2 provides a representative scheme of an OECT-based biosensor for the detection of a breast cancer cell biomarker. Above: the gate electrode modification processes for the detection of the HER2 protein biomarker and breast cancer cells. Below: the fabrication process of the multifunctional nanoprobe with high electrochemical activity.
Figure 3:
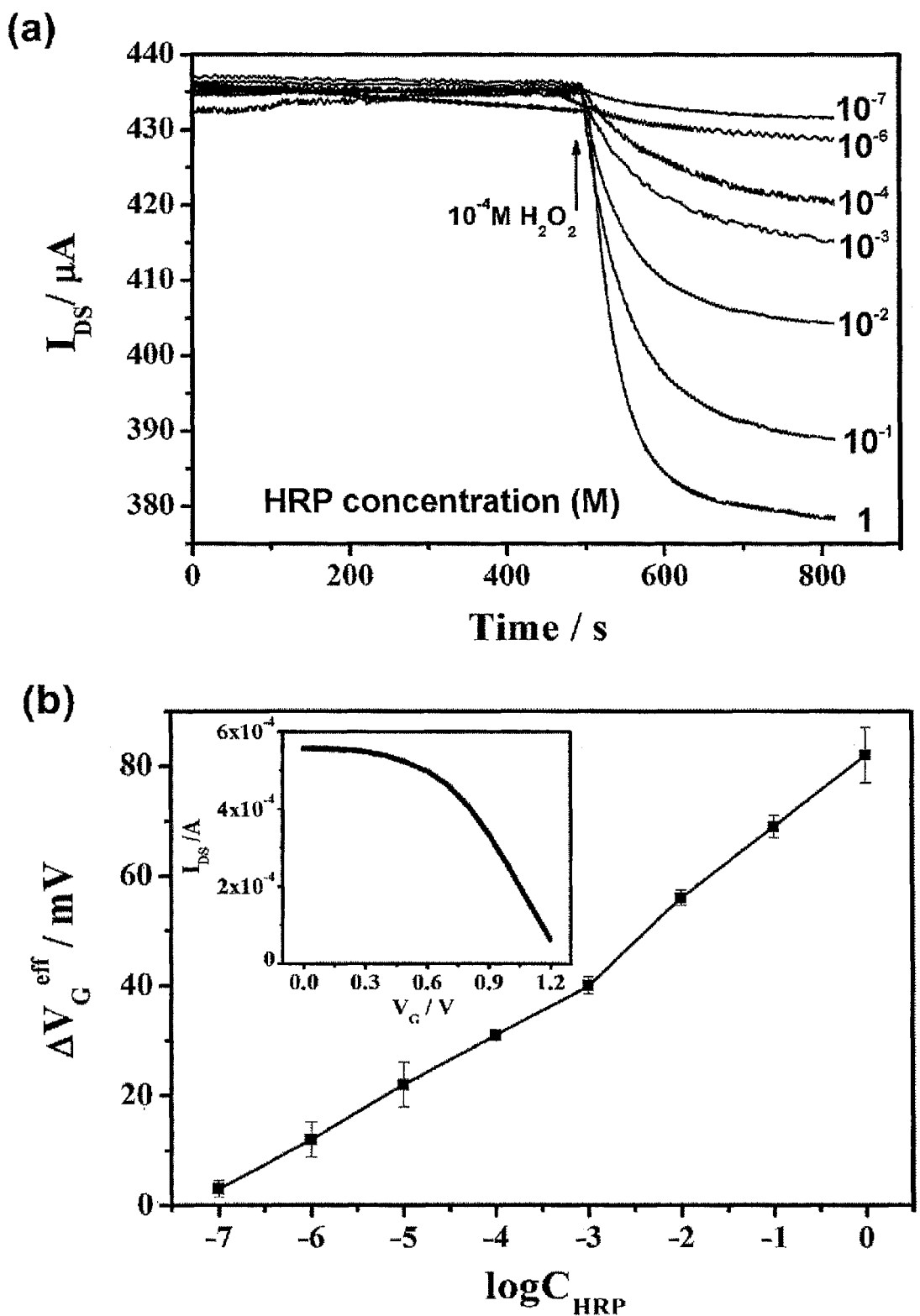
FIG. 3 shows the influence of the HRP enzyme on the electrochemical activity and the performance of OECTs with HRP/MAA/Au gate electrodes. (a) Channel current ($I_{DS}$) responses of OECTs to the addition of $10^{-4}$ M $H_2O_2$ in PBS solution. The gate electrodes of the OECTs are functionalized in HRP solutions with the concentrations changed from $10^{-7}$ to 1 M, i.e. $10^{-7}$, $10^{-6}$, $10^{-5}$, $10^{-4}$, $10^{-3}$, $10^{-2}$, $10^{-1}$, 1 M. (b) The change of the effective gate voltage $\Delta V_G^{eff}$ as a function of HRP concentration during gate modification.

To demonstrate the effect of HRP enzyme on the performance of OECTs, the Au gate electrodes of the OECTs were first modified with HRP. As shown in FIG. 2, an Au electrode is modified with mercaptoacetic acid (MAA) and HRP sequentially to get a HRP/MAA/Au electrode. The Au gate electrodes were treated in HRP solutions with different concentrations ($10^{-7}$ to 1 g mL$^{-1}$) for 5 h. It is reasonable to expect that the amount of HRP on an Au gate electrode increases with the increase of HRP concentration in the solution for modification. Then the OECTs were characterized in PBS solutions with the addition of $H_2O_2$ at the concentration of $10^{-4}$ M. FIG. 3a shows the responses of the devices to the addition of $H_2O_2$ measured at the same operation voltages ($V_{DS}$=0.05 V and $V_G$=0.6 V). It is notable that the current response increases with the increase of HRP concentration. According to the channel current change and the transfer curve of each device, the change of the effective gate voltage of the device induced by the reaction of $H_2O_2$ is calculated and presented in FIG. 3b. An increase in the effective gate voltage change $\Delta V_G^{eff}$ was observed with the increase of HRP concentration and the detection limit (signal/noise ratio≥3) of the device to the concentration of HRP in a solution is about $10^{-7}$ g mL$^{-1}$.

Figure 4:
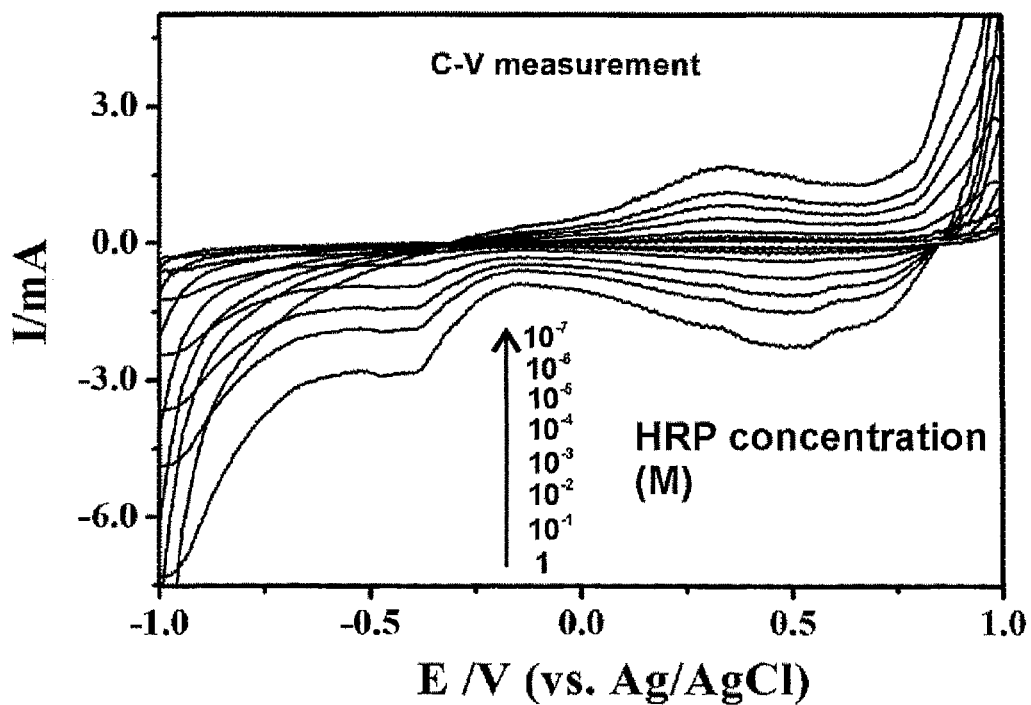
FIG. 4 shows the influence of the HRP enzyme on the electrochemical activity and the performance of OECTs with HRP/MAA/Au gate electrodes. (a) C-V measurement of the Au gates modified with HRP characterized in $10^{-4}$ M $H_2O_2$ PBS solutions. HRP concentrations changed from $10^{-7}$ to 1 M, i.e. $10^{-7}$, $10^{-6}$, $10^{-5}$, $10^{-4}$, $10^{-3}$, $10^{-2}$, $10^{-1}$, 1 M. (b) Redox peak current as a function of HRP concentration during the modification of Au electrodes.
Figure 4:
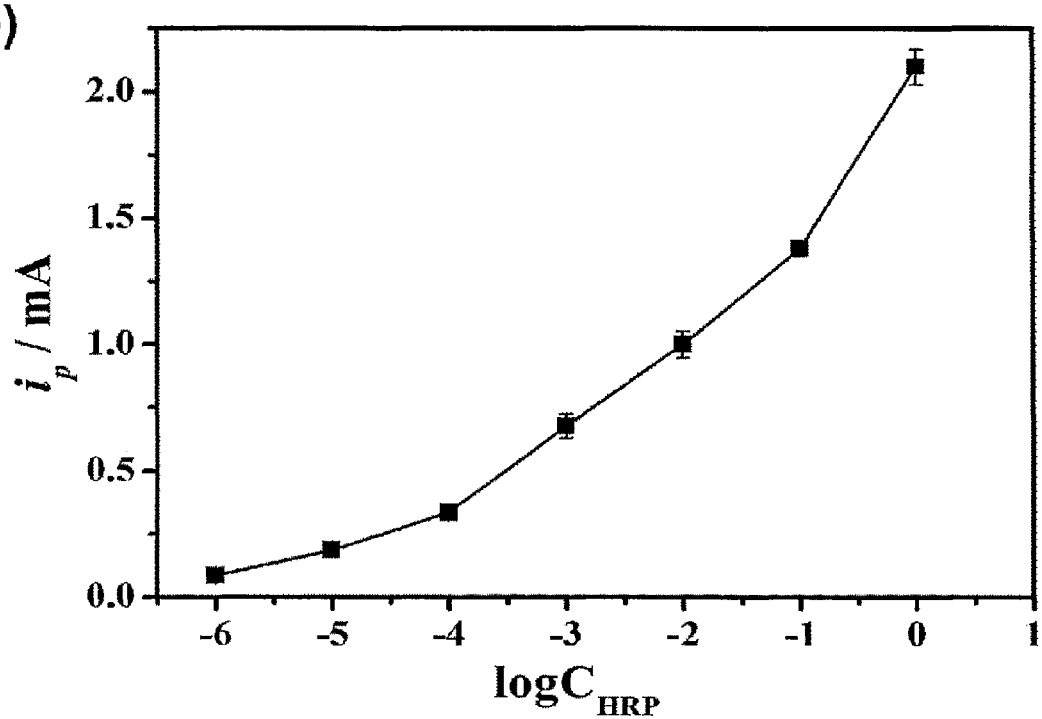

In comparison, the HRP-modified Au electrodes were then characterized with the conventional cyclic voltammogram (C-V) method, as shown in FIG. 4a. A current peak can be observed at the bias voltage of about −0.4 V and the peak current $i_p$ increases with the increase of HRP concentration, as shown in FIG. 4b. It is notable that the minimum concentration of HRP in solutions that can be detected by measuring C-V curves is about $10^{-5}$ g mL$^{-1}$, indicating that OECT-based protein sensors are much more sensitive than typical C-V measurements. Considering that the redox peak current $i_p$ is proportional to the density of HRP ($W_{HRP}$) modified on the gate electrode according to Equation (2), FIG. 4b also presents the relationship between the density of HRP on the gate and the concentration of HRP in PBS solution for electrode modification. Based on these results, the change of the effective gate voltage $\Delta V_G^{eff}$ as a function of [HRP] amount can be schematically presented by plotting $\Delta V_G^{eff}$ against $i_p$. It can be found that $\Delta V_G^{eff}$ is proportional to $Log(i_p)$ in a certain region, which is consistent with Equation (4). The slope is smaller in the low concentration region of HRP, indicating that the device is more sensitive at low concentrations. This result is similar to cases for many other OECT-based biosensors reported before, such as glucose, dopamine, and uric acid sensors. The performance of the HRP sensor laid the foundation for the devices of the present invention to detect biomarkers in the following experiments.

As an example, human epidermal growth factor receptor 2 (HER2) is a key prognostic biomarker for the determination of therapeutic treatment for breast cancer patients. HER2 was captured on the surface of the gate electrode of an OECT by an antibody and then specifically modified with catalytic nanoprobes. The sensing mechanism of the device is attributed to the electrochemical reaction catalyzed by the nanoprobes on the gate. It was found that a weak electrochemical reaction on the gate electrode can result in an obvious change in the effective gate voltage of the transistor and thus lead to a pronounced response of channel current. The device could specifically detect HER2 down to the level of $10^{-14}$ g/mL ($10^{-16}$ M), which is several orders of magnitude lower than the values obtained from conventional electrochemical approaches. The protein sensors are able to differentiate breast cancer cells from normal cells by measuring both cell lysates and living cells. Therefore, the OECT-based sensors can serve as a versatile platform for highly sensitive biomarker assays.

FIG. 2 shows the design of the gate electrode of an OECT-based sensor. The Au gate electrode is modified first with a specific HER2 antibody ($Ab_{Capture}$) that is used to capture HER2 proteins in solutions. In this example, the monoclonal anti-HER2 antibody was used as $Ab_{Capture}$ for binding with HER2 with high affinity and selectivity. With this capture component, the gate electrode could be specifically modified with HER2 even in the present of interference. In the next step, the captured HER2 was modified with catalytic nanoprobes because HER2 proteins are not electrochemically active. The nanoprobes used in this example are Au nanoparticles with a diameter of ~10 nm, which are modified with a HER2 detection antibody ($Ab_{Detection}$) and an electrochemically active HRP enzyme. The $Ab_{Detection}$ used in this example is polyclonal Anti-HER2 antibody, which can selectively bind with HER2 without affecting the binding between HER2 and $Ab_{Capture}$. Consequently, more HER2 protein captured on the gate electrode leads to more HRP enzyme on the gate.

Figure 5:
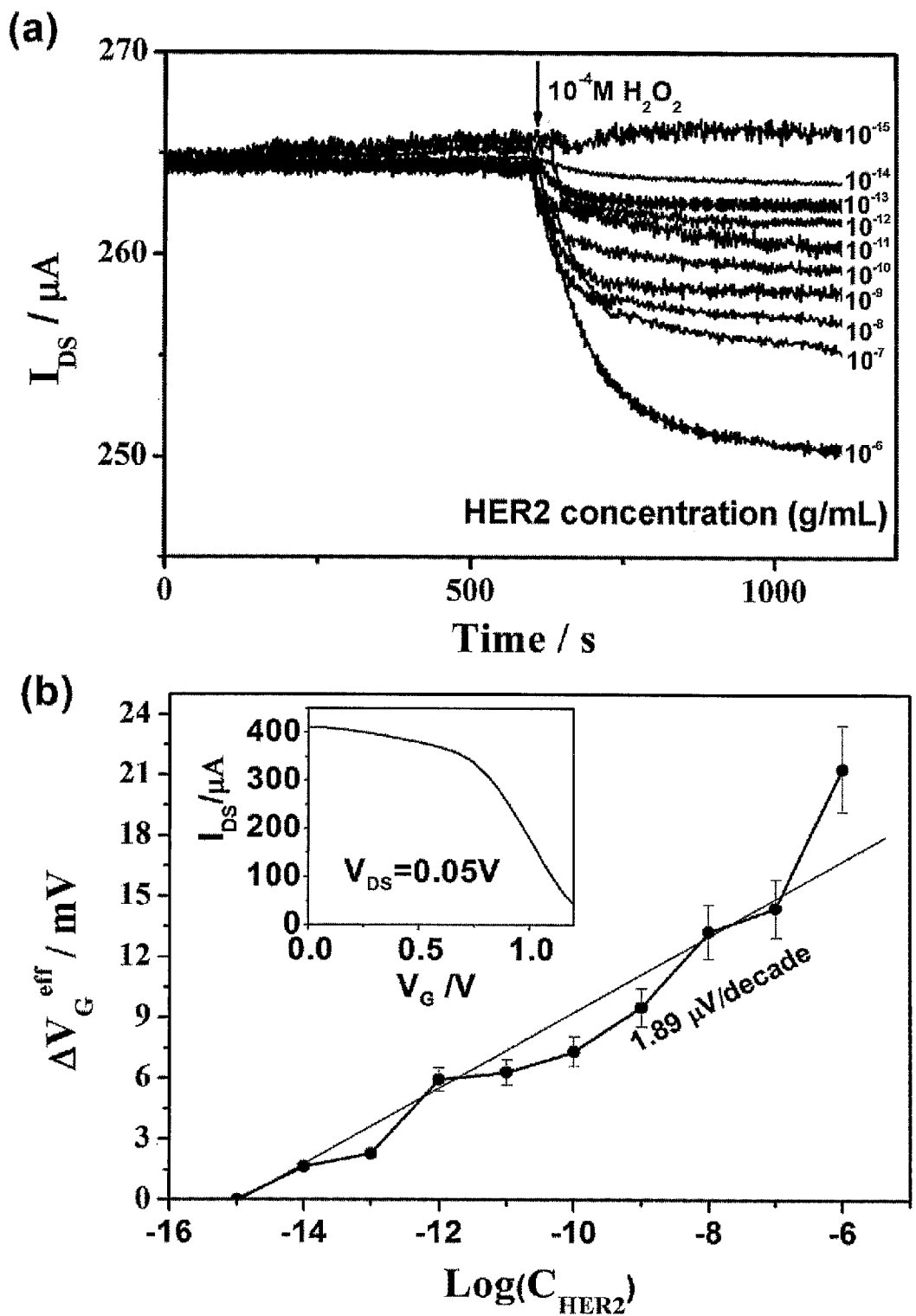
FIG. 5 shows OECT-based protein sensors with nanoprobes/HER2/Ab$_{Capture}$/MAA/Au gate electrodes for the detection of the cancer cell biomarker HER2. (a) The channel current responses of the devices to the addition of $H_2O_2$ at the operational voltages of $V_G$=0.6 V and $V_{DS}$=0.05 V. HER2 concentrations changed from $10^{-6}$ to $10^{-15}$ g mL$^{-1}$, i.e. $10^{-6}$, $10^{-7}$, $10^{-8}$, $10^{-9}$, $10^{-10}$, $10^{-11}$, $10^{-12}$, $10^{-13}$, $10^{-14}$, $10^{-15}$ g mL$^{-1}$. (b) The change of effective gate voltage ($\Delta V_G^{eff}$) induced by the reaction of $H_2O_2$ on the gate electrodes.
Figure 6:
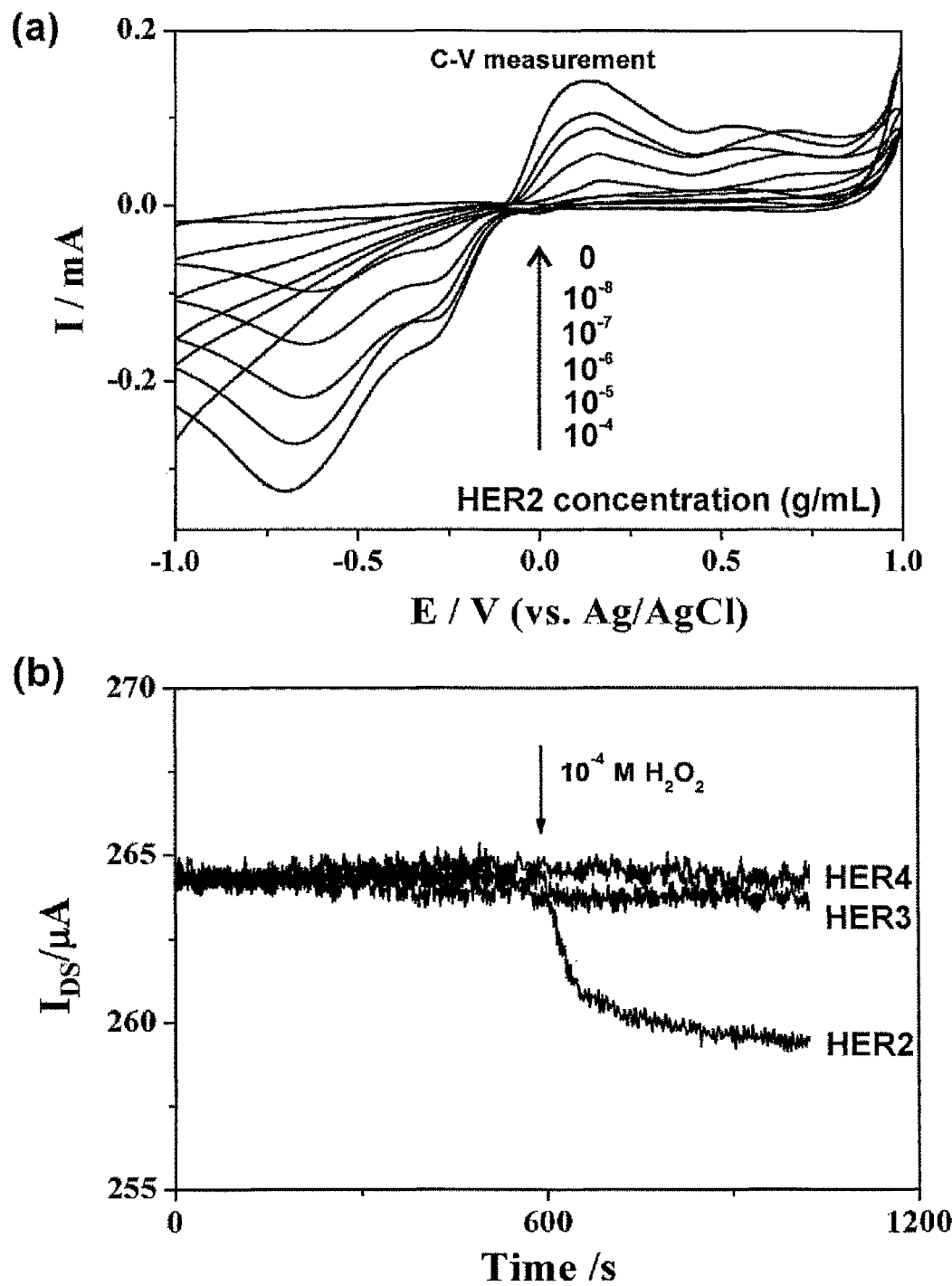
FIG. 6 shows OECT-based protein sensors with nanoprobes/HER2/Ab$_{Capture}$/MAA/Au gate electrodes for the detection of cancer cell biomarker HER2. (a) C-V curves of the Au gates of the devices characterized in $10^{-4}$ M $H_2O_2$ PBS solutions. HER2 concentrations changed from $10^{-4}$ to 0 g mL$^{-1}$, i.e. $10^{-4}$, $10^{-5}$, $10^{-6}$, $10^{-7}$, $10^{-8}$, 0 g mL$^{-1}$. (b) Current response of the OECT-based biomarker sensors modified with different proteins, including HER2 (response), HER3 (no response), and HER4 (no response).

The gate electrodes with the sandwiched structure of nanoprobes/HER2/$Ab_{Capture}$/MAA/Au were modified with HER2 protein and electrochemically active nanoprobes. Since a significant number of protein biomarkers in physiological environments have normal levels in ng mL$^{-1}$ or even pg mL$^{-1}$ range, the OECT biosensors should demonstrate a detection limit lower than this range to accurately differentiate the normal levels of cancer-free patients and the elevated levels indicative of cancer. HER2 protein solutions with concentrations ranging from $10^{-6}$ to $10^{-15}$ g mL$^{-1}$ were tested by using the devices. FIG. 5a shows the channel current responses of the devices to additions of $10^{-4}$ M $H_2O_2$ in PBS solutions. The lower the concentration of protein solution used for gate modification, the lower the channel current change ($I_{DS}$) observed, indicating that the electrochemical activity on the gate electrode is dependent on the protein concentration monotonically. The channel current change increases with the increase of protein level and demonstrates a good linear response (R=0.9898) in a wide concentration range ($10^{-7}$ to $10^{-14}$ g mL$^{-1}$). According to the channel current response, the change of effective gate voltage $\Delta_G^{eff}$ of the device is calculated, which also demonstrates a linear relationship with the protein concentration on a logarithmic axis, as shown in FIG. 5b. The detection limit of the device is about $10^{-14}$ g mL$^{-1}$ at the condition of a signal to noise ratio higher than 3. Therefore, the OECT-based protein sensors are sensitive enough to detect the HER2 expression levels both in normal and cancer patients even using a small amount of sample. The ultralow detection limit of the protein sensor could be attributed to the inherent amplification function of the OECTs. In comparison, the HER2 modified gate electrodes were used as working electrodes in electrochemical C-V measurements (FIG. 6a). The detection limit of HER2 protein in the C-V measurements is only about $10^{-8}$ g mL$^{-1}$, which is nearly 6 orders poorer than that of the OECT-based HER2 protein sensor. More importantly, the OECT-based HER2 sensors are much more sensitive than the reported electrochemical approaches in the literature, which normally exhibit a detection limit higher than $10^{-13}$ g mL$^{-1}$.

Figure 11:
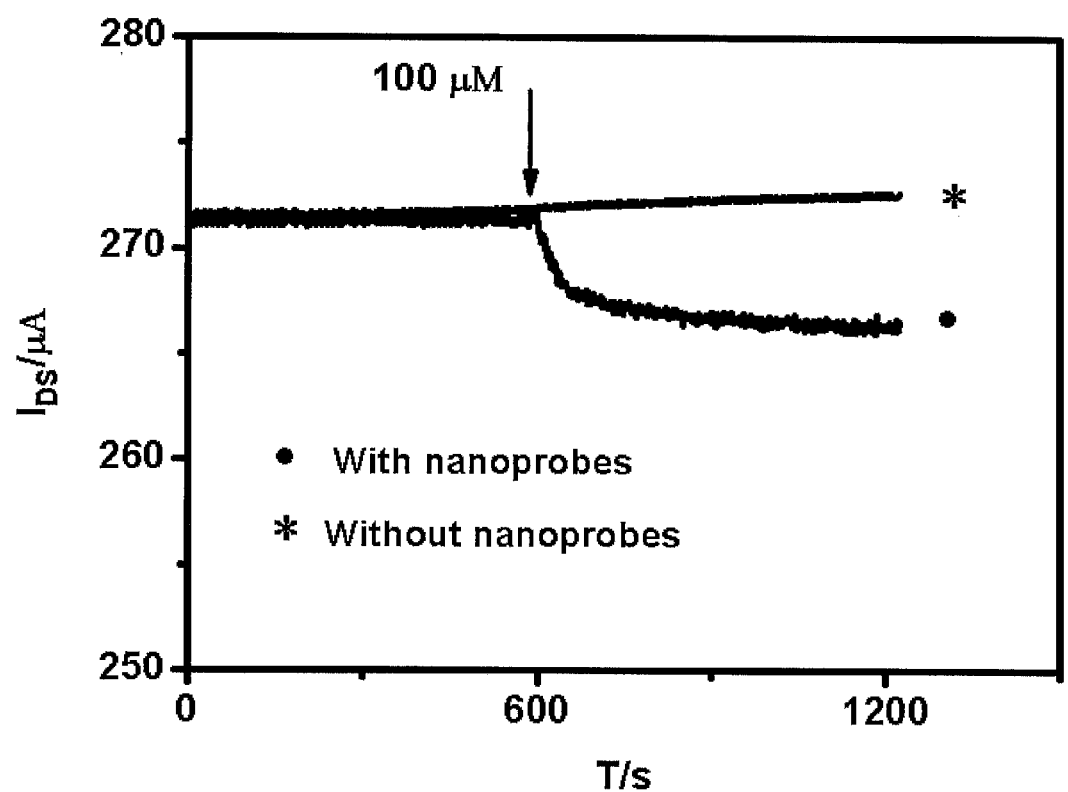
FIG. 11 provides an example of channel current responses of the OECT-based biosensors with or without the modification of nanoprobes on the gates.

To validate the effect of labelling nanoprobes, devices with or without modification of the nanoprobes were characterized in PBS solutions. The preparation conditions of the two devices at other steps were controlled to be identical. Both devices were modified with HER2 protein by incubating HER2 PBS solutions ($10^{-10}$ g mL$^{-1}$) on the Au gate electrodes for 2 h. The device labelled with nanoprobes demonstrated a significant decrease in channel current when $10^{-4}$ M $H_2O_2$ was added, while the device without nanoprobes showed no obvious response upon the addition of $H_2O_2$ (FIG. 11). The results clearly confirm that the nanoprobes on the gate electrodes of OECTs play a key role on the device response to the addition of $H_2O_2$. Since the concentration of the nanoprobes is proportional to the concentration of HER2 proteins captured on the gate electrodes of OECTs, the channel current responses can be used to identify the concentrations of HER2 proteins in tested solutions after calibration.

Figure 12:
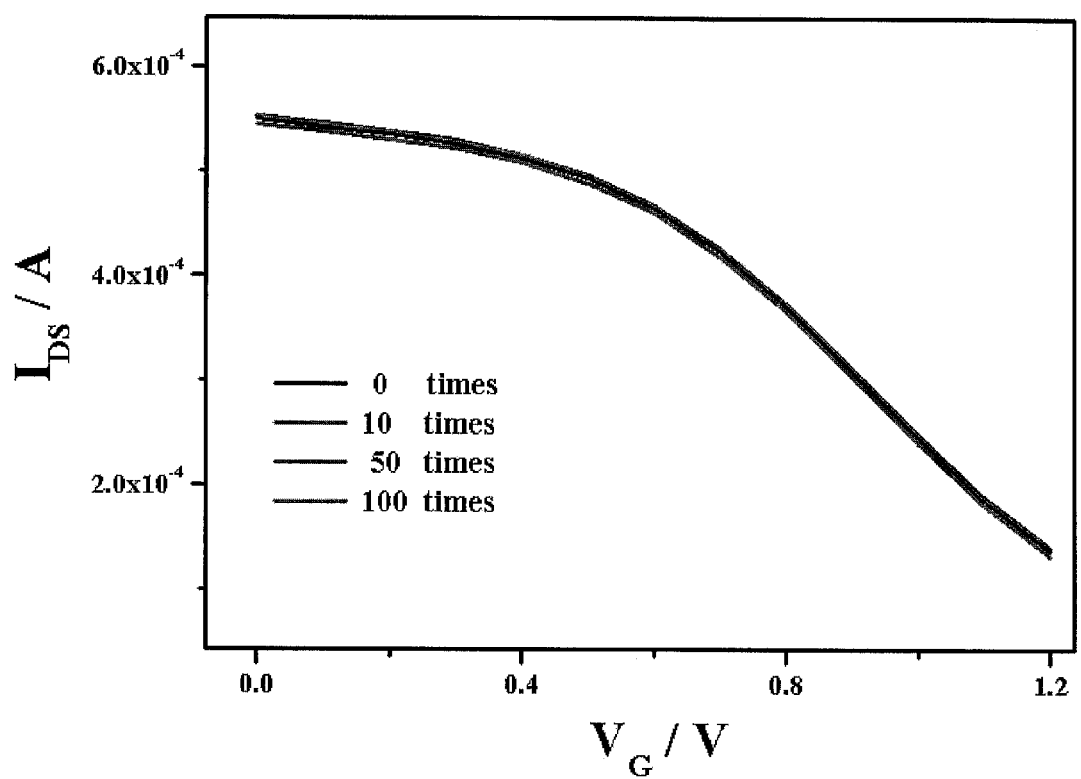
FIG. 12. The transfer characteristics of an OECT measured in PBS solution up to 100 times.

Selectivity is a significant consideration for cancer cell biomarker sensors. Human serum is a complex medium consisting of a myriad of biological elements and chemicals. Devices lacking selectivity would not be able to accurately and specifically differentiate the expression levels of HER2 protein in cancer cells and normal cells. To elucidate the selectivity of the functionalized OECT biosensor, HER2 was replaced with other members of the HER family, HER3 and HER4, with the same concentration in PBS solution in the procedure of device modification while other steps and conditions were kept unchanged. FIG. 6b demonstrates the channel current responses of the sensors treated with HER2, HER3, and HER4 protein solution. The OECT treated with HER2 protein solution displays an obvious current drop upon $H_2O_2$ addition, while the control devices demonstrate no detectable response. These results indicate that HER2 protein serves as the specific bridge to covalently connect the $Ab_{Capture}$ layer and the nanoprobe outer layer in the sandwiched modification technique of the gate electrode. Without the HER2 layer, the multifunctional nanoprobes used in the next step would be easily rinsed away during the gate preparation procedure. As discussed above, the absence of nanoprobes on the gate electrodes would not induce a response in channel currents when $H_2O_2$ was added. Therefore, the OECT-based biosensor is highly specific for HER2 biomarker detection. This device also shows good stability during measurements in PBS (FIG. 12).

Figure 7:
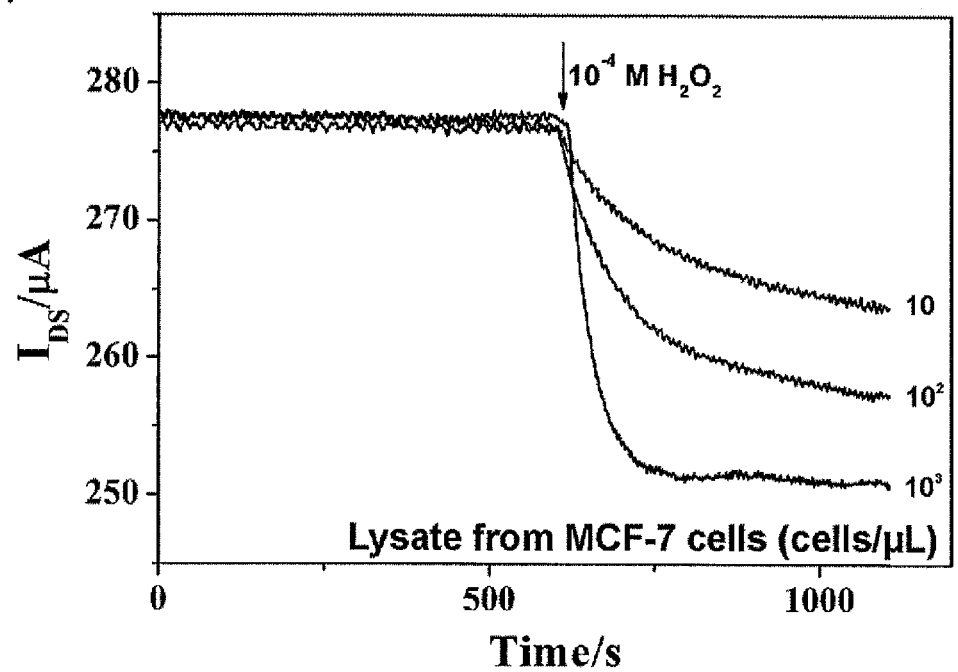
FIG. 7 shows OECT-based protein sensors for the detection of cancer cells. (a) Current responses of OECTs modified with the lysate of MCF-7 cancer cells to the additions of $10^{-4}$ M $H_2O_2$. $V_G$=0.6 V and $V_{DS}$=0.05 V. MCF-7 cancer cells concentrations are: $10^3$, $10^2$ and 10 cells (b) Current responses of OECTs modified with the lysate of normal cells NIH/3T3 (control devices). NIH/3T3 cells concentrations are: $10^3$, $10^2$ and 10 cells μL$^{-1}$.
Figure 7:
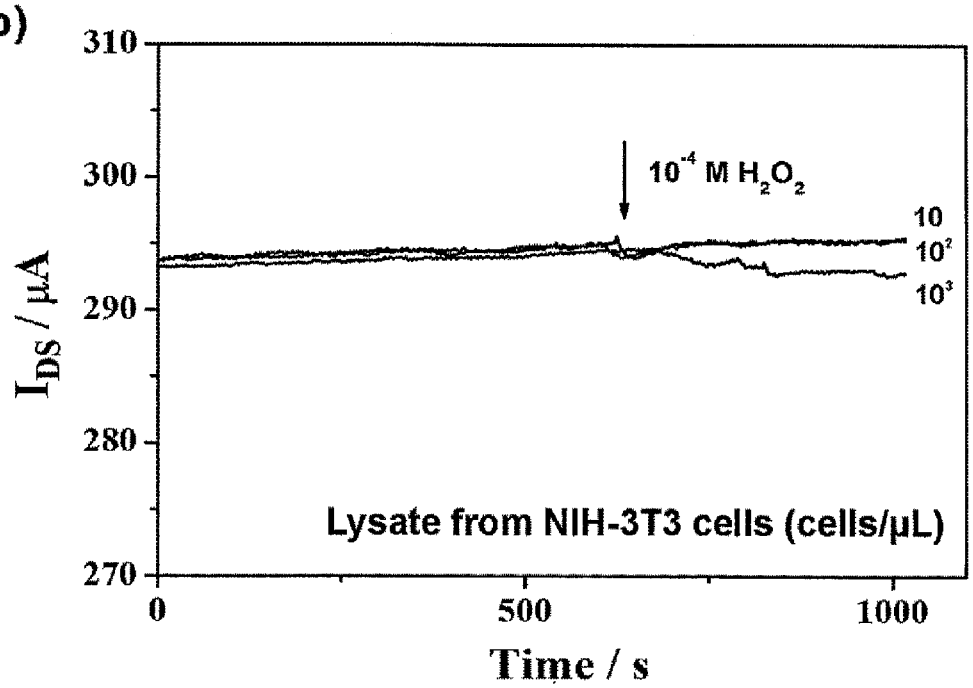

The OECT-based biosensors were used to differentiate breast cancer cells from normal cells to demonstrate the accuracy of the devices in real biomedical analysis. Lysates of two types of cells were tested; MCF-7 and NIH/3T3. MCF-7 cell is a breast cancer cell line primarily used in breast cancer research, while NIH/3T3 cell (mouse embryonic fibroblast cell) is the standard normal cell line used for control experiments. It has been reported that the expression levels of HER2 are higher in cancer cells than in normal cells. In the gate modification procedure shown in FIGS. 1 and 2, cell lysate solutions were used to replace the HER2 protein solution, while the other steps are unchanged. Different densities of cells from 10 to $10^3$ cells $\mu L^{-1}$ were tested in the experiments. FIG. 7a demonstrates the channel current responses of the OECTs modified with the MCF-7 cell lysate to the additions of $10^{-4}$ M $H_2O_2$ in PBS solutions. OECTs modified with the breast cancer cell lysates show significant responses to the addition of $H_2O_2$ and the channel current change increases with the increase of cell density. FIG. 7b shows the response of the control group modified with the normal NIH/3T3 cell lysate. The responses induced by $H_2O_2$ addition are relatively low in comparison with devices modified with the cancer cell lysates. Even when the NIH/3T3 cell lysate of $10^3$ cells $\mu L^{-1}$ solution was used in device modification, the channel current response is much lower than that observed in devices for sensing cancer cells, indicating the lower expression level of HER2 in NIH/3T3 cell than in cancer cells.

Figure 13:
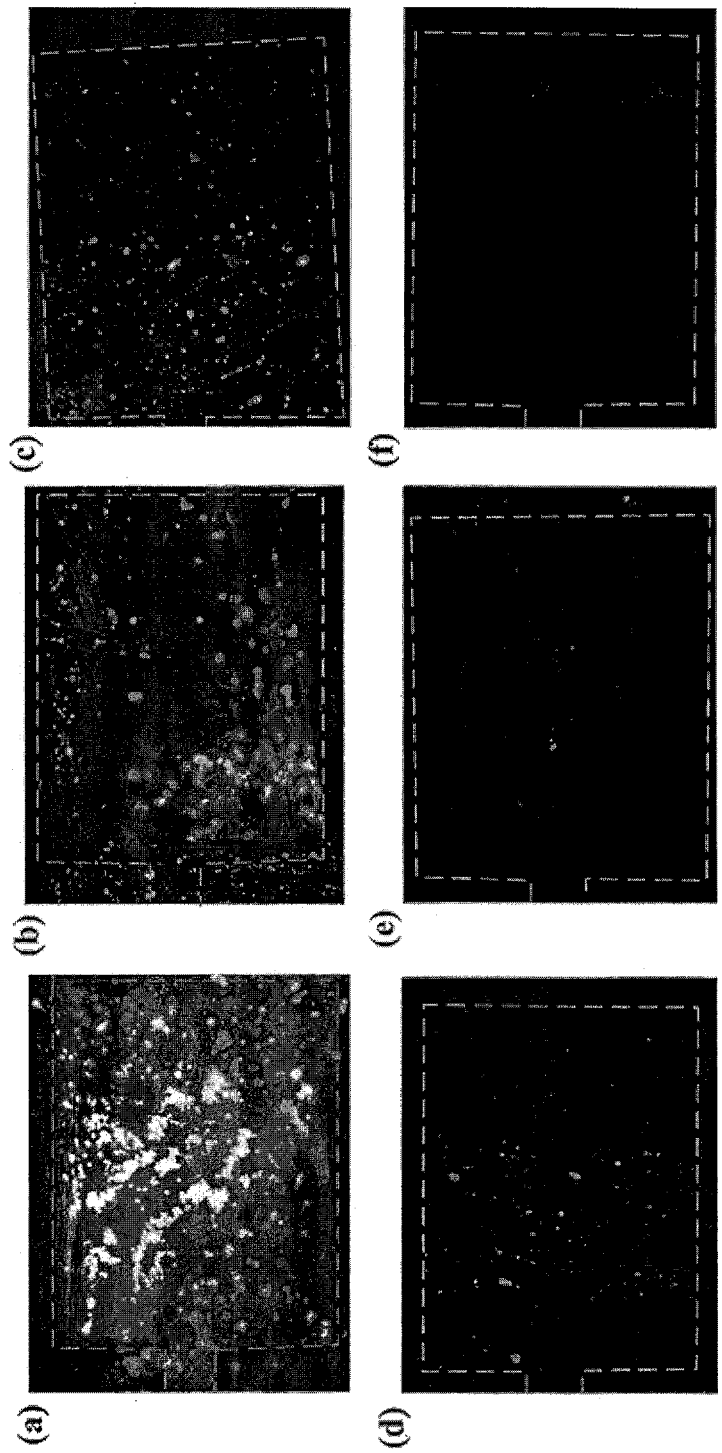
FIG. 13. Fluorescence images of MCF-7 and NIH/3T3 cells (stained with SYTO green fluorescent nucleic acid stain from Thermo Fisher Co. at 37° C. for 15 min) captured on $Ab_{capture}$-modified Au gate electrodes. The dashed lines represent the boundaries of the Au electrodes. (a-c) The gate electrode was modified with MCF-7 cancer cells with different solution concentrations, including: (a) $10^3$ cell/µL (b) $10^2$ cell/µL (c) 10 cell/µL. (d-f) The gates modified with NIH/3T3 normal cells with different solution concentration, including (d) $10^3$ cell/µL (e) $10^2$ cell/µL (f) 10 cell/µL.
Figure 14:
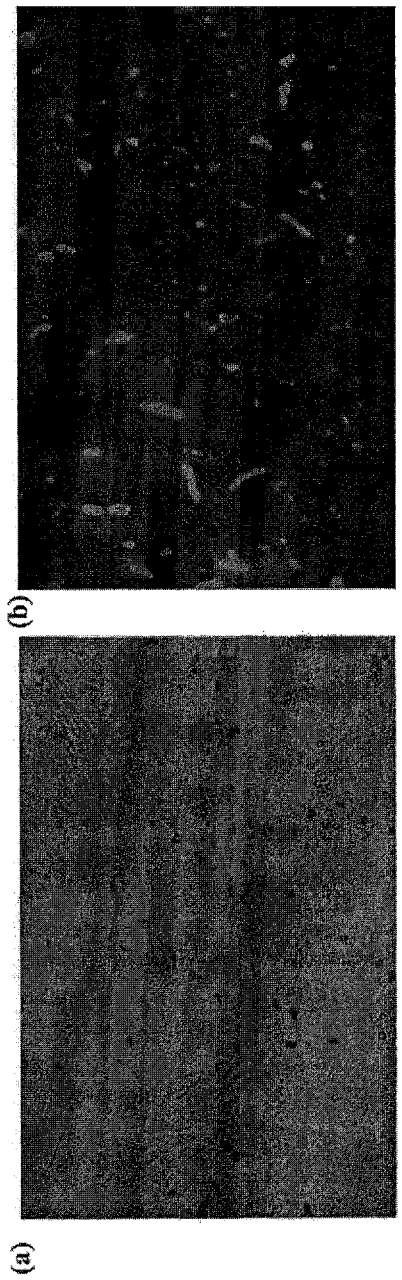
FIG. 14. (a) Optical image and (b) high resolution fluorescence image of MCF-7 cancer cells captured on an $Ab_{capture}$-modified Au gate electrode.

The protein sensors were used to directly test living cells in the next step. Because cancer cells have more HER2 proteins on their membranes than normal cells, cancer cells have a higher possibility of being captured by the HER2 antibody on the Au gate electrode (FIGS. 13 and 14).

Figure 8:
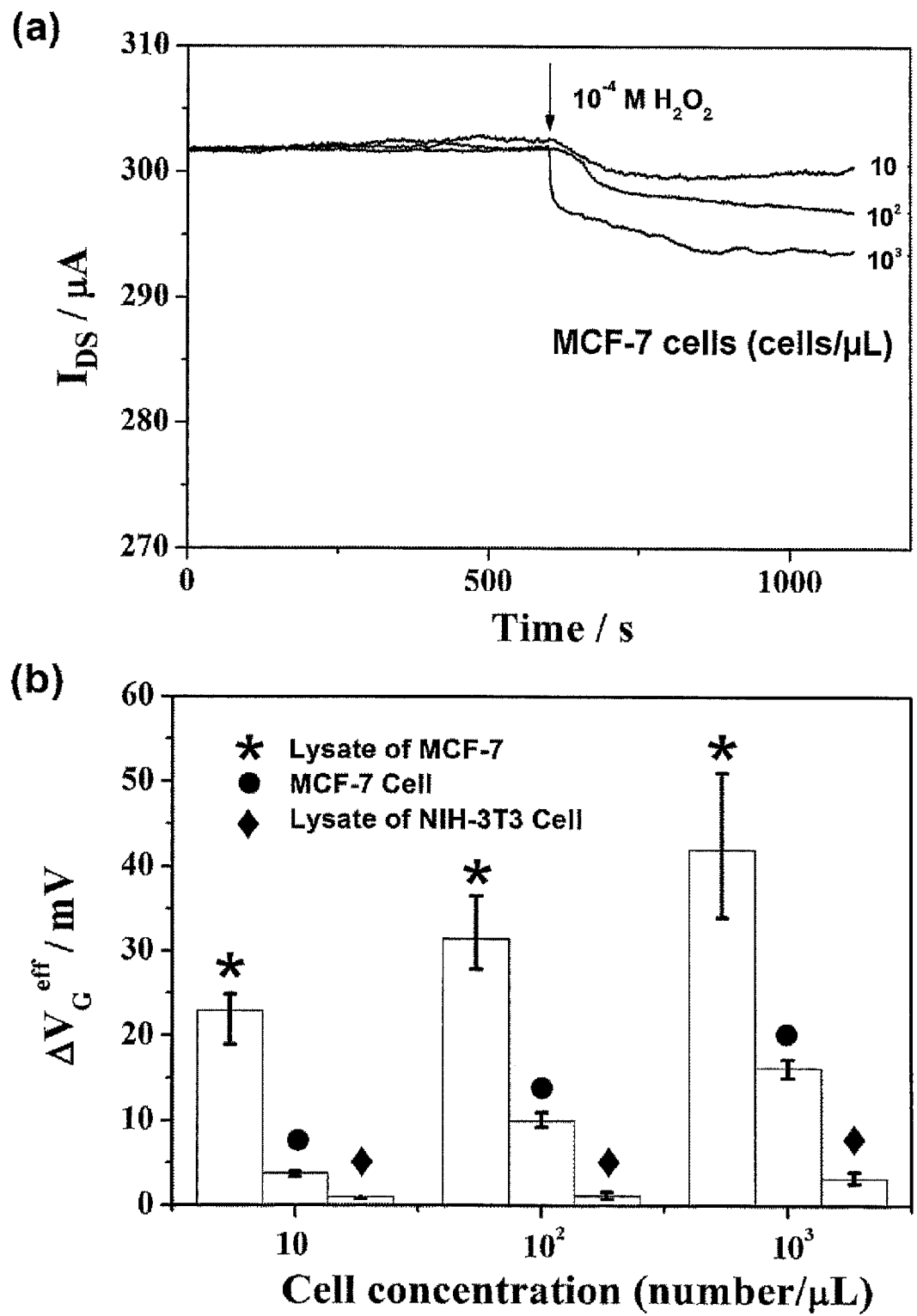
FIG. 8 shows OECT-based protein sensors for the detection of cancer cells. (a) Current responses of OECTs modified with MCF-7 cells on the gates. MCF-7 cancer cells concentrations are: $10^3$, $10^2$ and 10 cells μL$^{-1}$. (b) The change of the effective gate voltage $\Delta V_G^{eff}$ for the devices modified with different cell lysates or whole cells. Error bars are calculated from at least 3 devices.
Figure 15:
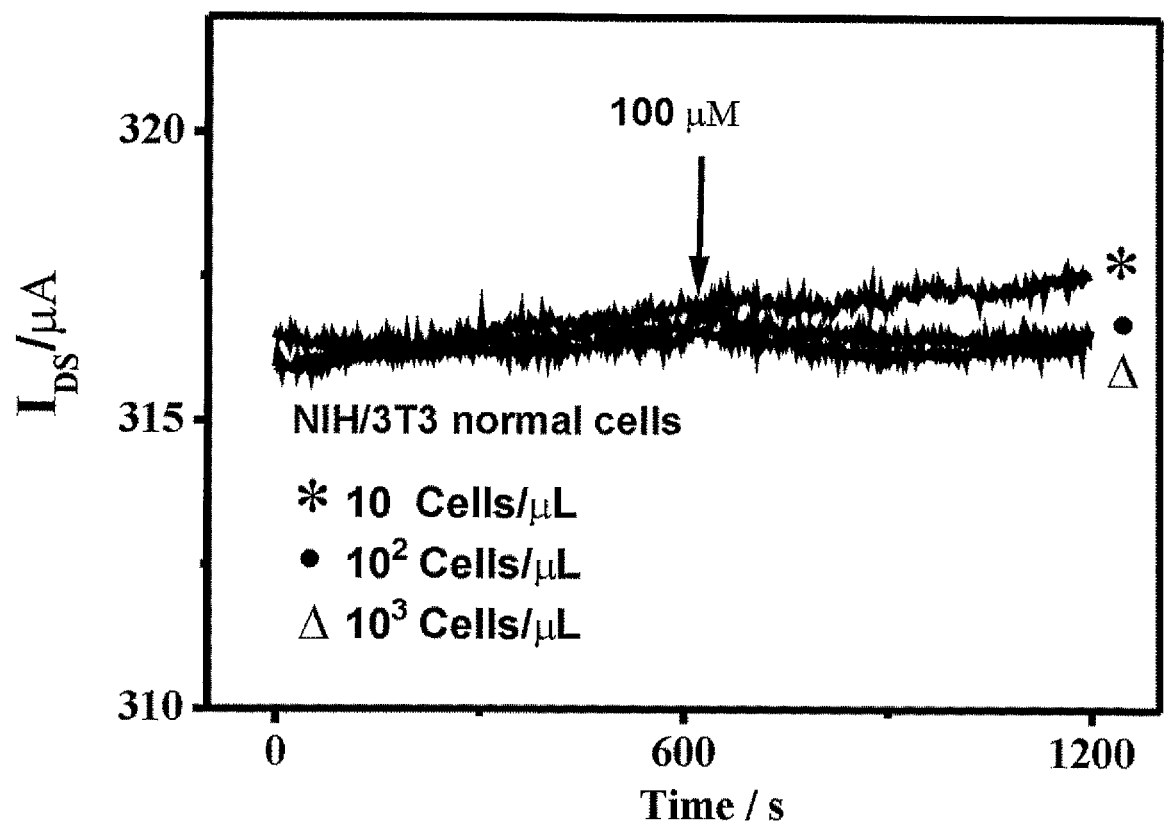
FIG. 15. Current responses of OECTs modified with NIH/3T3 cells on the gates.

On the other hand, a higher density of HER2 protein on cancer cells will enable labelling of the nanoprobes with a density higher than that on normal cells. As shown in FIG. 8a, the biosensors modified with MCF-7 cancer cells demonstrate obvious responses in channel currents upon $H_2O_2$ addition and the current change increases with the increase of cell density in the tested cell solutions. In contrast, the devices modified with NIH/3T3 normal living cells demonstrate negligible response to $H_2O_2$ addition even for a high concentration cell solution ($10^3$ cells $\mu L^{-1}$) because normal cells are difficult to capture by the antibody $Ab_{Capture}$ (FIG. 15).

The OECTs could differentiate the breast cancer cells from normal cells in the tests.

According to the channel current responses, the changes of effect gate voltage $\Delta V_G^{eff}$ induced by the reaction of $H_2O_2$ on the gates can be calculated. FIG. 8b shows $\Delta V_G^{eff}$ of the devices modified with different cell lysates or cells. It is obvious that the responses of the devices treated with cancer cells are much larger than that of the devices modified with normal cell lysate. Therefore, the functionalized OECTs can serve as high-performance protein biomarker sensors for highly sensitive and selective detection of HER2 in cancer cells. It is notable that $\Delta V_G^{eff}$ of the devices modified with living cells is smaller than that of the devices modified with cell lysates prepared from the same concentration of cells, which can be attributed to the fact that HER2 protein inside living cells cannot be detected in the former case. For living cancer cells, only a limited proportion of HER2 protein located on the surface of cell membrane could react with the antibody and serve as the bridge to capture the catalytic nanoprobes. Therefore, the devices modified with cell lysates are able to load a larger amount of nanoprobes on the gate electrode leading to larger responses.

Successful use of OECTs as highly sensitive biosensors for the detection of protein cancer biomarkers has been demonstrated herein. The gate electrodes of the devices are modified with an antibody that can selectively capture the target protein. By further modifying the protein on the gate electrodes with catalytic nanoprobes, the devices show obvious current responses to additions of $H_2O_2$ and the magnitude of current response increases with the increase of protein concentration in the detected solution. The devices can specifically detect a cancer biomarker HER2 down to the level of $10^{-14}$ g $mL^{-1}$, which is several orders of magnitude lower than those of conventional electrochemical approaches. The OECT protein sensors demonstrate responses to a wide range of HER2 protein levels, from $10^{-14}$ to $10^{-7}$ g $mL^{-1}$, which is sensitive enough to detect a trace amount of HER2 level both in breast cancer cells and normal cells. Based on this strategy, the electrochemical biosensors were successfully used to differentiate cancer cells from normal cells with excellent selectivity in testing either a cell lysate or living cells. The sensing mechanism of the protein sensor is attributed to the monotonically increased electrochemical activity on the gate electrode with the increase of analyte concentration. The obtained results demonstrate that OECTs are a versatile platform for disposable, flexible, and highly sensitive analyte biosensors.

Preparation of Nanoprobes

A brief exemplary summary of the preparation of AuNPs is as follows; 500 mL of 1 mM $HAuCl_4$ was brought to a rolling boil with vigorous stirring. After rapid addition of sodium citrate (38.8 mM, 50 mL) to the vortex, the solution changed color from pale yellow to burgundy and the AuNPs were obtained. The pH of the Au nanoparticle solution was adjusted to 9.0 with $K_2CO_3$ (0.2 M). The nanoprobes ($Ab_{detection}$-Au-HRP bioconjugates as example) were freshly prepared by adding $Ab_{detection}$ (2 mg $mL^{-1}$, 1 mL) and HRP (6 mg $mL^{-1}$, 1 mL) into the PBS solution with AuNPs (1.0 mL) with gentle mixing for 2 h. The remaining active AuNPs surface on the nanoprobe was then blocked by BSA via the treatment of BSA solution (1%, 1 mL) for 30 min. The solution was then centrifuged for 10 min at 10,000 rpm, and the supernatant was removed. The nanoparticles were washed with PBS solution for further purification and separated as above. The resulting nanoprobes were re-dispersed in PBS and stored at 4° C. prior to use in the device fabrication procedure.

Preparation of Enhanced Nanoprobes

Multiwall nanotubes (MWNT) solution were well dispersed in 20 wt. % poly(diallyldimethylammonium chloride) solution and treated with ultrasonication for 30 mins. Prepared AuNPs were then added and reacted for 5 h. after washed with water solution, $Ab_{detection}$ (2 mg/mL, 1 mL) and HRP (6 mg/mL, 1 mL) were added with gentle mixing for 2 h. The enhanced nanoprobes were re-dispersed in PBS and stored at 4° C. prior to use in the device fabrication procedure.

Device Fabrication

FIG. 2 shows an exemplary schematic diagram of the OECT based protein sensor. Patterned Au (~100 nm)/Cr (~10 nm) source, drain and gate electrodes were firstly deposited on a glass substrate using magnetron sputtering with the aid of a shadow mask. The thin chromium layer serves as an adhesive layer to improve the adhesion of the Au layer on the substrate. Then the substrates with patterned electrodes were treated with $O_2$ plasma (5 mins), followed by the spin-coating of PEDOT:PSS (3000 rpm) layer onto the confined channel area between source and drain (0.2×6 mm). The PEDOT:PSS coated devices were transferred to a glove box filled with high purity of $N_2$ for annealing at 200° C. for 1 hour.

Gate Electrode Modification with HRP

Au gate electrodes (0.3 cm×0.3 cm) were immersed in Piranha solution ($H_2O_2/H_2SO_4$, V/V=3/1) and then polished to obtain mirror surface with 0.5 um alumina power, followed by sonication in ethanol and water respectively. MAA (50 mM, 10 µL) were modified on the clean gate electrode in the dark overnight to give carboxyl groups, a 10 µL of a mix-solution of EDC (0.2 mM, in MES pH5.5 solution) and NHS (0.5 mM, in MES pH5.5 solution) was introduced to the electrode surface to activate the carboxyl groups to bind with HRP for 5 h with different concentrations respectively. At last, the electrode was incubated with BSA solution (1%, 1 mL) for blocking and washed with PBS for three times.

Gate Electrode Modification with Protein

Au gate electrodes (0.3 cm×0.3 cm) were firstly immersed in Piranha solution ($H_2O_2/H_2SO_4$, V/V=3/1) and then polished to obtain mirror surface with 0.5 um alumina power, followed by sonication in ethanol and water respectively. MAA (50 mM, 10 µL) were modified on the clean gate electrode in dark overnight to give carboxyl groups, a 10 µL of a mix-solution of EDC (0.2 mM, in MES pH5.5 solution) and NHS (0.5 mM in MES pH5.5 solution) was introduced to the electrode surface to active the carboxyl groups to bind with $Ab_{capture}$. Therefore, $Ab_{capture}$ (2 mg/mL, 10 µL) was then immobilized on the gate for 5 h and BSA solution (1%, 1 mL) was further added for 30 min to block the remaining nonspecific binding sites of the Au electrode. After washing the $Ab_{capture}$-modified gate electrode carefully, HER2 in PBS solutions with different concentrations were incubated on the gate electrode for 2 h, followed by another wash of PBS solution. In the end, 10 µL of nanoprobes were added on the gate electrode for 2 h to label the captured HER2 to give electrochemical activity.

Gate Electrode Modification with RNA

Clean Au gate electrodes (0.3 cm×0.3 cm) were incubated with 100 mM SH-DNA overnight and washed with ethanol. Mercaptoethanol solution (1%, 1 mL) was then further added for 30 min to block the remaining nonspecific binding sites of the Au electrode. The electrode was modified with different concentrations of miRNA and then washed with PBS three times. Signal DNA and nanoprobes were then incubated on the miRNA modified electrode, respectively. The well-modified electrodes were then stored carefully at 4° C. before use.

Gate Electrode Modification with Enhanced Nanoprobes

Similar to the above modification process, the enhanced nanoprobes replaced the nanoprobes used in modification in the last step. Before use, the enhanced nanoprobes were sonicated for 15 mins to avoid aggregation.

Device Characterization and Detection

OECT protein sensors were immersed in PBS buffer solution in the measurements of transistor performance. Source, drain and gate electrodes were connected to two Keithley measurement units (Keithley 2400). The gate voltages ($V_G$) and source-drain voltages ($V_{DS}$) were set by the Labview program. To characterize the responses of the gate-functionalized transistors with different biomarkers, a designated amount of $H_2O_2$ solution ($10^{-4}$ M) was added into the PBS solution to induce the electrochemical reaction. The protein sensor was measured at fixed gate and drain voltages ($V_G$=0.6 V and $V_{DS}$=0.05 V). The added $H_2O_2$ reacted with the HRP enzyme on the nanoprobes, which in turn modifies the channel current $I_{DS}$ at fixed operational voltages. The detection limit of each device was defined by the channel current response with the condition of signal/noise>3. The transfer characteristic, i.e. channel current $I_{DS}$ as a function of gate voltage $V_G$ at a fixed $V_{DS}$ (0.05 V), of each OECT sensor was also measured, in a gate voltage range 0 to 1.2 V at a sweeping rate of 0.02 V s$^{-1}$.

Since the biomarker concentration change in the early stages of disease is subtle, it requires detection assays with high sensitivity to detect low-abundance biomarkers. Compared with the low sensitivity of present technology, the OECT is an ideal candidate for the sensing part since a transistor is the combination of a sensor and an amplifier. It is suitable for ultrasensitive sensing of low-abundance biomarkers in clinical application.

The nanoprobe also plays an important role in the high sensitivity and selectivity of the device. It is fabricated by combining recognition segments and HRP on gold nanomaterials. The nanomaterials with a large surface area enable a large loading of HRP. The recognition segments such as, for example, antibodies and capture DNA can selectively bind with biomarkers even in a complex environment (for example, a cancer cell lysate, blood, body fluids, etc.).

The advantages of the present device are as follows: 1. compared with existing technology like western blotting, gel electrophoresis and RT-PCR, it can accomplish selective biomarker analysis with a simple detection process and a very low detection limit; 2. compared with existing technology like mass spectrometry, it can achieve biomarker analysis in living cells without a devastating sample preparation process and expensive, complex instrumentation; 3. the biosensors of the present invention are portable while existing techniques are not portable; 4. the devices of the present invention are low cost in comparison with existing approaches.

The devices of the present invention can be further optimized for a higher sensitivity. The gate electrode area in the OECT device can be optimized to have a better detection performance. Devices with the same channel area but a different size of the gate electrode can be fabricated since the size of the gate electrode is critical to the sensitivity of the OECT. The channel size of the exemplary OECT is W/L=5 mm/0.1 mm. The gate area can be designed to be 1, 2, 5, 10, 20, 50 and 100 times of the channel area of the OECT. An optimum size of the gate electrode can be decided after the devices are characterized in electrolytes (PBS, pH 7.2).

The viscosity of PEDOT:PSS aqueous solution for spin coating is important for the quality of the coated film of channel. Therefore, the viscosity of the solution can be controlled by adding glycerol, which has high viscosity, or water, which has low viscosity. The thickness of the coated PEDOT:PSS film needs to be controlled since the film thickness is an important factor that can influence the response time and sensitivity of the sensors.

To generate the electrochemical signal, the HRP in the nanoprobes reacts with the added $H_2O_2$ and is immobilized on the gate electrodes. The concentrations of HRP can be varied according to the needs of the user of the invention. Transfer and output characteristics of the OECTs may also be varied according to the requirements of the user. Such characterization conditions include the applied voltage, sweeping rate and waiting time.

Figure 10:
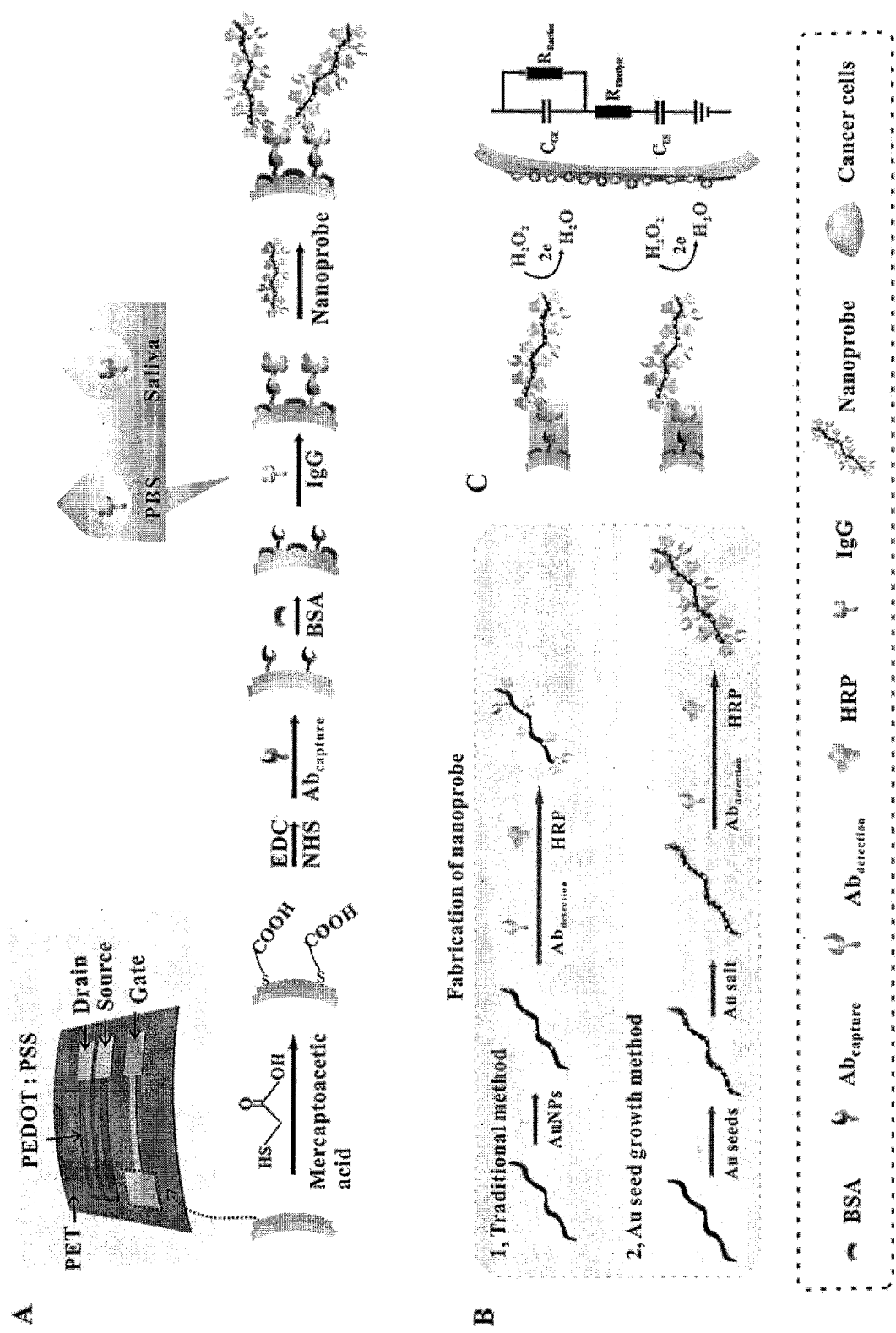
FIG. 10 provides an example of an ultra-sensitive OECT sensor for a biomarker (Immunoglobulin G) with a signal amplification strategy based on an enhanced nanoprobe.

In addition, the device could be further developed as an ultra-sensitive organic electrochemical transistor sensor for biomarkers (Immunoglobulin G is provided herein as an example) with a signal amplification strategy based on an enhanced nanoprobe (FIG. 10).

Although antibodies and nucleic acid probes are described herein as exemplary binding agents, the skilled person will recognise that the present invention encompasses any suitable binding agent which can act as a recognition agent and bind with a high enough affinity to the analyte of interest to capture the analyte on the surface of the gate electrode and/or nanoparticle. In some embodiments of the present invention, the first and/or second binding agent may be a monoclonal antibody, a polyclonal antibody, an antibody fragment or an antigen. In other embodiments, the first and/or second binding agent may be a DNA or RNA oligonucleotide.

The electrodes used in the exemplary embodiments are patterned gold/chromium electrodes. The person skilled in the art will recognise that these electrodes may be substituted with electrodes fabricated using other substances, for example, platinum. Carbon-based electrodes such as graphite electrodes could also be used. The organic semiconductor used in the channel may also be selected from a range of suitable semiconducting polymers, and the viscosity of the semiconducting polymer may be varied in a number of ways, for example, by the addition of glycerol or water. The organic semiconductor may be applied as a film coating between the source and drain electrodes.

Horseradish peroxidase was used herein as an exemplary electrochemically active enzyme, with hydrogen peroxide as the substrate for the enzyme. The present invention could be used with any suitable enzyme-substrate reactions which involve the transfer of electrons.

The nanoparticles of the present invention used to increase the rate of electron transfer may be gold, but the invention is not limited to the use of gold nanoparticles. The diameter of the nanoparticles may be varied according to the requirements of the user.

The width and length of the channel between the source and gate electrodes may also be varied by users of the invention, as may the surface area of the gate electrode. The person skilled in the art may vary the ratio of the surface area of the gate electrode to the surface area of the channel to optimise the device for their requirements.

The devices and methods of the present invention may be used to detect an analyte in a cell lysate or in whole cells. The sample could be a cell culture, a medical sample such as blood, serum, saliva or urine, a sample of food or an environmental sample. The ability to use the present invention with samples of living cells provides an advantage over existing methods of detecting analytes, such as mass spectrometry, which require extensive sample degradation. The analyte may be a protein or a nucleic acid. In some embodiments, the analyte is a miRNA.

The person skilled in the art will also recognise that the methods of the present invention may be varied and that the signals generated may be processed and displayed in many different ways. In some embodiments, the signal generated may be compared with that generated by a control sample. This method could be used in the diagnosis and/or prognosis of a wide range of diseases and/or medical conditions.

Although the detailed description above conveys exemplary embodiments of the present invention in sufficient detail to enable those of ordinary skill in the art to practice the present invention, features or limitations of the various embodiments described do not necessarily limit other embodiments of the present invention, or the present invention as a whole. Hence, the detailed description above does not limit the scope of the present invention, which is defined only by the claims.

REFERENCES

M. A. Ali, K. Mondal, Y. Jiao, S. Oren, Z. Xu, A. Sharma, and L. Dong, *ACS Appl. Mater. Interfaces*, 2016, 8, 20570.

Payne R C A J, Anderson-Mauser L, Humphreys J D, Tenney D Y, Morris D L. Automated Assay for HER-2neu in Serum. *Clin Chem* 46, 175-182 (2000).

M. J. van de Vijver, J. L. Peterse, W. J. Mooi, P. Wisman, J. Lomans, O. Dalesio, R. Nusse, *N. Engl. J. Med.* 1988 319, 1239.

G. Somlo, S. K. Lau, P. Frankel, H. B. Hsieh, X. Liu, L. Yang, R. Krivacic, R. H. Bruce. *Breast Cancer Res Treat.* 2011, 128, 155.

R. H. Yolken, *Rev. Infect. Dis.* 1982, 4, 35.

G. Frens, Controlled nucleation for the regulation of the particle size in monodisperse gold suspensions. *Nature*, 1973, 241(105): 20-22.

The aforementioned references are hereby incorporated by reference in their entirety.

INDUSTRIAL APPLICABILITY

The objective of the presently claimed invention is to provide devices that achieve highly sensitive detection of biomarkers with a simple detection process and at low cost. The claimed invention can be used for the detection of various analytes in various samples of interest and for the detection of various biomarkers in clinical analysis by simply changing the corresponding recognition segments.

The invention claimed is:

1. An electrochemical biosensor comprising a plurality of electrodes, comprising:
   a gate electrode comprising a first agent capable of specifically binding to an analyte in a sample;
   a source electrode;
   a drain electrode;
   a channel comprising an organic semiconductor between the source electrode and the drain electrode;
   a plurality of gold nanoparticles comprising an electrochemically active enzyme and a second agent capable of specifically binding to the analyte in the sample; and
   a substrate for the electrochemically active enzyme,
   wherein the gate electrode and the channel are separated by an electrolyte, and wherein the electrolyte contacts the gate electrode and the channel.

2. The electrochemical biosensor according to claim 1, wherein at least one of the first agent or the second agent is an antibody.

3. The electrochemical biosensor according to claim 1, wherein the first agent is a monoclonal antibody capable of specifically binding to the analyte.

4. The electrochemical biosensor according to claim 1, wherein the first agent is a nucleic acid probe capable of specifically binding to the analyte.

5. The electrochemical biosensor according to claim 1, wherein the second agent is a polyclonal antibody capable of specifically binding to the analyte.

6. The electrochemical biosensor according to claim 1, wherein the electrochemically active enzyme is horseradish peroxidase and the substrate for the electrochemically active enzyme is hydrogen peroxide.

7. The electrochemical biosensor according to claim 1, wherein the organic semiconductor comprises a film coating on the drain and source electrodes.

8. The electrochemical biosensor according to claim 1, wherein the organic semiconductor comprises poly (3,4-ethylenedioxythiophene) polystyrene sulfonate (PEDOT: PSS).

9. The electrochemical biosensor according to claim 1, wherein at least one of the plurality of electrodes further comprises gold.

10. The electrochemical biosensor according to claim 1, wherein the gate electrode comprises grooves comprising the first agent capable of specifically binding to an analyte.

11. The electrochemical biosensor according to claim 1, wherein the nanoparticles have a diameter of under 90 nm, under 80 nm, under 70 nm, under 60 nm, under 50 nm, under 40 nm, under 30 nm, under 20 nm, under 10 nm, or under 1 nm.

12. The electrochemical biosensor according to claim 1, wherein the channel has a width of 5 mm and a length of 0.1 mm.

13. The electrochemical biosensor according to claim 1, wherein the sample is selected from a cell lysate or whole cells, and wherein the analyte is selected from protein or nucleic acid.

14. The electrochemical biosensor according to claim 13, wherein the analyte is microRNA (miRNA).

15. A method for detecting an analyte in a sample, the method comprising contacting the sample in the electrochemical biosensor according to claim 1 to produce a measurable signal.

16. The method according to claim 15, wherein the detecting further comprises contacting a control sample in the electrochemical biosensor to produce a measurable signal and comparing the measurable signal of the sample with the measurable signal of the control sample.

17. The method according to claim 15, wherein the analyte is a biomarker and the detecting comprises at least one of the diagnosis or prognosis of a disease or medical condition.

18. The method according to claim 17, wherein the disease or medical condition is cancer.

19. The method according to claim 18, wherein the cancer is breast cancer.

20. The method according to claim 17, wherein the biomarker is human epidermal growth factor receptor 2 (HER2).

21. The electrochemical biosensor according to claim 1, further comprising a plurality of multiwall nanotubes, wherein the plurality of nanoparticles are disposed on the surface of the plurality of multiwall nanotubes.

* * * * *